United States Patent [19]
Tolliver

[11] 3,959,660
[45] May 25, 1976

[54] IR GENERATOR HAVING ELLIPSOIDAL AND PARABOLOIDAL REFLECTORS

[75] Inventor: Peter Marvin Tolliver, Brighton, N.Y.

[73] Assignee: Sybron Corporation, Rochester, N.Y.

[22] Filed: Jan. 29, 1973

[21] Appl. No.: 327,693

Related U.S. Application Data

[63] Continuation-in-part of Ser. No. 295,421, Oct. 6, 1972, Pat. No. 3,784,836.

[52] U.S. Cl. ............................ 250/504; 250/304; 250/341; 250/343; 250/492 R
[51] Int. Cl.² ..................................... G01J 1/00
[58] Field of Search .......... 250/494, 504, 493, 496, 250/503, 495; 240/41.35 R; 350/294, 492, 493, 494

[56] References Cited
UNITED STATES PATENTS

| 1,867,502 | 7/1932 | Edstrom ...................... 240/41.35 R |
| 2,647,203 | 7/1953 | Smith .......................... 240/41.35 R |
| 3,405,268 | 10/1968 | Brunton ............................. 250/339 |
| 3,437,804 | 4/1969 | Schaefer et al. ............. 240/41.35 R |

Primary Examiner—Harold A. Dixon
Attorney, Agent, or Firm—Theodore B. Roessel; Joseph C. MacKenzie

[57] ABSTRACT

An infrared generator wherein an ellipsoidal reflector has a source rich in infrared radiation at one focus thereof. The end of the reflector at the other focus merges with a paraboloidal reflector positioned so that the focus of the latter reflector coincides with the said other focus of the former. The axes of the reflectors intersect, preferably at right angles to each other.

2 Claims, 5 Drawing Figures

IR GENERATOR HAVING ELLIPSOIDAL AND PARABOLOIDAL REFLECTORS

RELATED APPLICATIONS

This application is a continuation-in-part of my earlier application Serial No. 295,421, filed Oct. 6, 1972, now patent No. 3,784,836, which issued on Jan. 8, 1974, assigned to the assignee hereof, and entitled "I.R. Generator Having Ellipsoidal and Paraboloidal Reflectors". This application is also an improvement on the invention disclosed and claimed in the application of John Charles Udart, Serial No. 327,692, having the same filing date title and assignee.

FIELD OF THE INVENTION

The present invention generally relates to measuring the properties or the nature of a given material as a function of the interaction of said material with infrared (IR) radiation. More particularly, the present invention relates to generating the IR radiation both efficiently and suitable for measuring moisture content of paper web by subjecting the paper to the infrared radiation and detecting the effect of moisture in the paper on the radiation. Measuring systems of the sort contemplated here are typified by the system described and claimed in U.S. Pat. No. 3,551,678 to Richard L. Mitchell.

Description of the Prior Art

Prior art IR radiation generators in the systems known to me are highly inefficient. Because the basic signal to noise ratio of a system is determined by the generator, such inefficiency is a major source of difficulty in designing a system which will be simultaneously suitable for on-line use of controlling industrial processes, and at the same time accurate.

It is the object of the present invention to provide, in a system of the Mitchell type, a novel high-efficiency IR radiation generator, so efficient as to increase markedly the measuring capability of the system and, simultaneously, to simplify the system and make it more rugged. It is also a particular object of the invention to provide an IR radiation generator which is efficient, light and compact, is easy and inexpensive to construct, and yet is simple in design, durable and rugged.

Summary of the Invention

According to the present invention, the novel IR radiation generator comprises an ellipsoidal reflective shell in combination with a paraboloidal reflective shell, the focus of the latter being coincident with a focus of the former, there being an IR-rich source of radiation at the other ellipse focus, and the major and principal axes of the shells intersecting at right angles to each other. The source IR radiation is collected by the ellipsoidal shell and the collected radiation is collimated by the paraboloidal shell.

In use according to the aforesaid Mitchell patent, the collimated IR is filtered to produce IR beams having well-defined spectral content. The beams are directed on the paper, or other material, and the system senses what remains of the beams after they have interacted with the paper, and then computes some property or characteristic of the material, for example, moisture content of the paper, that is to say, the percent by weight of liquid water contained in that portion of the paper irradiated by the IR beams. In the present invention, 70% or more of the IR from the source is collimated and presented for filtering, an improvement of about one order of magnitude on the prior art.

DESCRIPTION OF THE PREFERRED EMBODIMENTS

Figure 1:
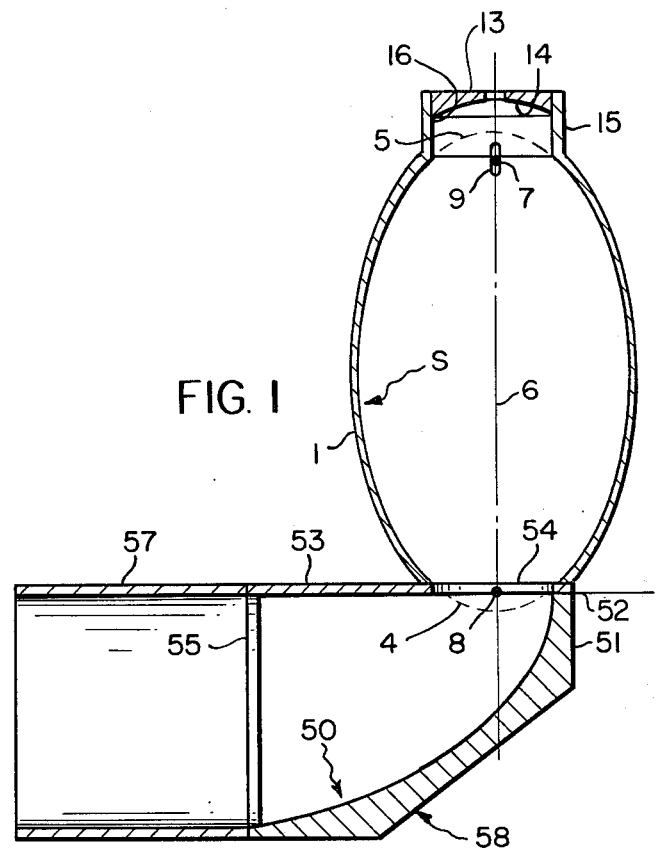
FIG. 1 is a side elevation, in section taken on line 1—1, FIG. 2, of an IR generator according to the invention.

In FIG. 1, reference numeral 1 denotes a shell having internal reflecting surface S coincident with an ellipsoidal surface of revolution of a plane ellipse about its major axis. As will be seen from FIGS. 1, 2 and 3, the shell corresponds to the surface truncated at both ends to define circular apertures. In FIG. 1, the missing ends are identified by dashed line segments 4 and 5, which, of course, also coincide with the aforesaid ellipse.

The major axis of the ellipse is denoted by reference numeral 6 and the ellipse's foci are denoted by reference numeral 7 and 8. Focus 7 is at the center of a filament 9, the length of which coincides with axis 6, and which forms part of a suitable lamp (now shown), which is supported in any suitable manner (not shown) by a reflector 13 having spherical reflecting surface 14, the radius of which coincides with the axis 6.

Reflector 13 closes the end of a cylinder 15 having an internal reflecting surface 16 the axis of which coincides with axis 6. The cylinder 15 and reflector 13 then together close the aperture 3 in shell 1.

For present purposes, filament 9 may be supposed to be an IR-rich source, when electrically energized to incandescence, as for example, in a quartz-iodine lamp, or equivalent. The purpose of the structure thus far described is to reproduce, so to speak, the radiation from the filament, a focus 8.

Supposing the surface S to be perfectly smooth and reflective with respect to the desired spectral content of the radiation from filament 9, then it is immediately obvious that when the filament incandesces, a great deal of the resultant radiation will be reflected substantially to focus 8, in practice around 70%. Naturally, for maximum efficiency optimum finish of reflecting surfaces is required. Thus, in the present case, the spectral range of interest went down to 1.8 micron wave-length. In order to achieve specular reflection at this wavelength, a 4 micron layer of gold was plated on surface S after the surface, originally produced by machining it out of a cylinder of brass, had been smoothed as much as possible by machining, buffing and the like.

According to the present invention, the radiation from the image source is collimated by a paraboloidal shell, the principal axis of which intersects the major axis of shell 1, preferably at a right angle thereto, and with focus 8 coinciding with the focus of the paraboloidal shell.

Figure 2:
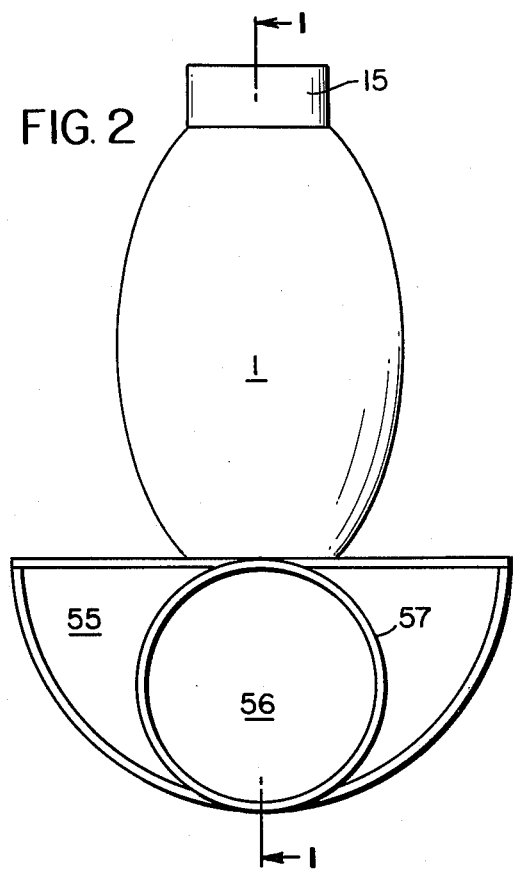
FIGS. 2 and 3 are an opposing end elevation and a plan view, respectively, of the IR generator of FIG. 1.

Thus, in FIG. 1 a shell 51 is coupled to shell 1, shell 51 having an internal reflecting surface 50 in the form of part of a paraboloidal surface of revolution corresponding to a parabola the focus of which is focus 8, and the principal axis of which is line 52 perpendicularly intersecting axis 6 at focus 8 and lying in the section plane corresponding to line 1—1 of FIG. 2.

LIke the Tolliver generator's paraboloidal shell, shell 51 collimates the radiation from, in effect, focus 8. However, due to the orientation of the principal axis 52, and with the relative proportions shown in the Figure, especially the length of shell 51, about 70% of the radiation reflected from the surface 50 is collimated, whereas the Tolliver generator of the earlier application, produces about 50% collimated light for the same length of paraboloidal shell.

Further, the shell 51 is semi-paraboloidal, being completed by a flat plate 53 having an aperture 54, the plane of which bisects the paraboloid corresponding to surface 50 along the principal axis of the paraboloid, and includes the focus 8 as a point thereof. Shell 1 is fixed to the plate 53 by any suitable means (not shown).

Finally, shell 51 is terminated by a semi-circular flat plate 55 having a circular aperture 56 therein, and a right circularly cylindrical tube 57 the bore of which coincides with aperture 56. Plate 55 and tube 57 are secured together and to shell 51 in any suitable manner.

The surfaces of tube 57 and plates 53 and 55 exposed directly or indirectly to light from filament 9 may be blackened in order to decrease the amount of non-collimated light exiting from tube 57. It will be observed that substantially all the light from filament 9 exits from the generator (and should, because light that does not exit would heat the generator structure, generally a undesirable result) although not entirely by way of focus 8. In any event, for measuring purposes, even the uncollimated light is effective, although less so than the collimated light. Accordingly, I prefer that the aforesaid surfaces of tube 57 and plates 53 (and, of course, the surfaces 50) have the same specular character as surface S.

The area of aperture 56 corresponds roughly to the portion of surface 51 most effective in collimating the light from aperture 54, which portion is substantially that visible through tube 57 in the view of FIG. 2. In practice, the aperture 56 would generally be chosen to have the same area and shape as the filter to be irradiated, and from that would be determined the constants of the paraboloid and ellipsoid corresponding to surfaces 50 and S of appropriate dimensions.

Figure 3:
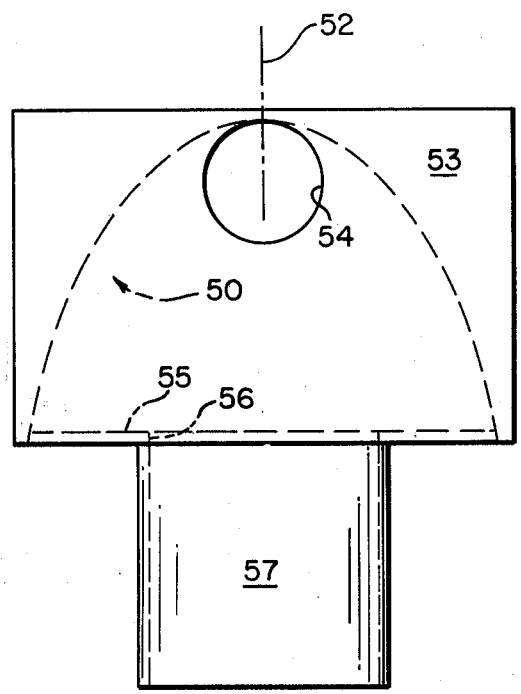

Inspection of FIGS. 1, 2 and 3 will show that the shell 51 is in essence a right circular cylinder, most of which was cut away to form the surface 50, and a substantial piece of which has been beveled away at 58 so as to leave a shell of very roughly uniform thickness and of semi-paraboloidal proportions.

Figure 4:
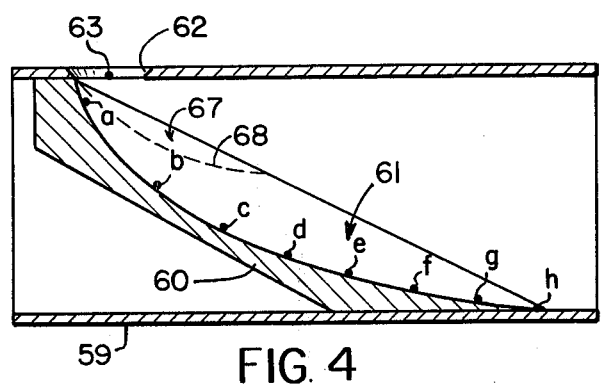
FIGS. 4 and 5 are views corresponding to FIGS. 1 and 2 but of a modified form of the IR generator of FIG. 1.
Figure 5:
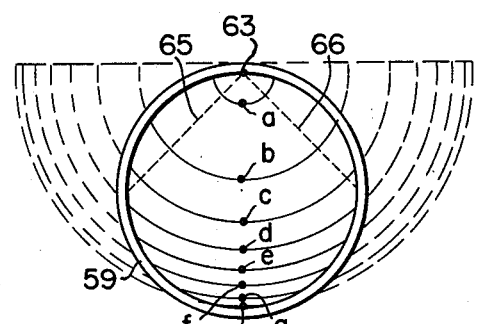

As shown in FIG. 4, the shell 51 can, in effect be reduced further to a shell 60. Shell 60 is essentially shell 51 lacking the portions visible outside the perimeter of tube 57 in FIG. 2. That is to say, shell 60 is a cylindrical insert in right circularly cylindrical tube 59, as shown in FIG. 5, wherein are shown contour lines $a$ through $h$ of the paraboloidal surface 61 (corresponding to that portion of surface 50 visible through tube 57 in the view of FIG. 2). Contour lines $a$ through $h$ are circular arcs, centered on the principal axis of surface 61, and lying in planes perpendicular to said axis and equi-spaced therealong. The focus of surface 61 is point 63 of the last said axis, and access to that focus is via an aperture 62 in the side of tube 59, centered on focus 63. Like the generator form of FIGS. 1, 2 and 3, the form shown in FIGS. 4 and 5 would be completed by an ellipsoidal shell 1 having a focus at 63 and fixed to tube 59 over aperture 62.

As will be seen from FIG. 5, inclusions of those parts of surface 61 outside the acute angular sector defined by dashed lines 65 and 66 requires surface 61 to take up half of a full paraboloid, although a quarter of a full paraboloid, such as would be subtended by planes perpendicular to the plane of FIG. 5 and containing lines 65 and 66, would have nearly as much paraboloidal surface. The surface difference would be twice that intended at 67, FIG. 4, above dashed line arc 68 of which dashed line 66, is the projection in FIG. 5. It would be within the present invention to use less than half the paraboloidal surface, a quarter for instance. The degree of collimation would be decreased, in proportion to the aforesaid surface difference, but if a net loss in total radiation be prevented by modifying the tube to fit a quarter shell, so that in one way or another all the light entering the cylinder 59 exits from the open end thereof, a quarter paraboloid will be almost as effective a light source for measurement purposes, as a half-paraboloid.

The terms full, half and quarter are to be understood as relative to sectioning in planes containing the principal axis of a paraboloid. There are obvious advantages in being able to make less than a full paraboloid do the job of a full one. Thus, if the paraboloidal surfaces are produced by machining it is obviously better to be able to start with one full paraboloid and cut it in two or more sections, in order to make two or more collimator surfaces, than to have to machine each of such surfaces as a full paraboloid.

Having described my invention as required by the statutes, I claim:

1. In an IR generator, the combination of a first shell having an inner reflective ellipsoidal surface and a second shell having an inner reflective paraboloidal surface;

said shells being secured together with one focus of said ellipsoidal surface being also the focus of said paraboloidal surface, said surfaces also having their respective major and principal axes intersecting each other;

said first shell being adapted for providing a source of radiation at the other focus of said ellipsoidal surface and said shells having openings where they are secured together, for allowing said radiation to enter said second shell via said one focus;

said paraboloidal surface being a semiparaboloid, and there being a cylindrical tube containing said second shell; said tube having one of said openings in the side thereof, and said second shell being oriented in said cylinder so that said focus of said paraboloidal surface is at said one of said openings and said principal axis thereof is along the length of said tube.

2. The invention of claim 1 wherein said axis are substantially perpendicular to each other.

* * * * *

PO-1050
(5/69)

UNITED STATES PATENT OFFICE
CERTIFICATE OF CORRECTION

Patent No. 3,959,660    Dated May 25, 1976

Inventor(s)  Peter Marvin Tolliver

It is certified that error appears in the above-identified patent and that said Letters Patent are hereby corrected as shown below:

Column 2, line 30, "now" should be --not--.

Column 2, line 43, "a" should be --at--.

Column 3, line 3, "LIke" should be -- Like --.

Signed and Sealed this

Tenth Day of August 1976

[SEAL]

*Attest:*

RUTH C. MASON
*Attesting Officer*

C. MARSHALL DANN
*Commissioner of Patents and Trademarks*